United States Patent [19]

Rossini et al.

[11] Patent Number: 4,819,316

[45] Date of Patent: Apr. 11, 1989

[54] METHOD OF MAKING A PRE-ADJUSTED ORTHODONTIC BRACKET ASSEMBLY

[75] Inventors: Robert S. Rossini, Arvada; Walter J. Steinhauser, Lakewood, both of Colo.

[73] Assignee: RMO, Inc., Denver, Colo.

[21] Appl. No.: 79,246

[22] Filed: Jul. 29, 1987

[51] Int. Cl.⁴ ............................................. B21F 43/00
[52] U.S. Cl. ..................................... 29/160.6; 29/412; 72/332; 83/620; 433/8
[58] Field of Search ....................... 29/160.6, 412, 414; 83/620; 433/8, 9, 16; 72/326, 332

[56] References Cited

U.S. PATENT DOCUMENTS

| | | | |
|---|---|---|---|
| 3,477,128 | 11/1969 | Andrews | 433/16 |
| 3,605,233 | 9/1971 | Rosiello | 29/160.6 |
| 3,922,787 | 12/1975 | Fischer et al. | 433/8 |
| 4,216,583 | 8/1980 | Reynolds | 433/9 |
| 4,415,330 | 11/1983 | Daisley et al. | 433/16 |
| 4,639,218 | 1/1987 | Jones et al. | 433/8 |
| 4,659,309 | 4/1987 | Merkel | 433/9 |

Primary Examiner—P. W. Echols
Attorney, Agent, or Firm—Sheridan, Ross & McIntosh

[57] ABSTRACT

A pre-adjusted orthodontic bracket assembly is provided. The assembly has one or two tie wings and a base pad. The tie wings define an archwire slot for alignment with the occlusal plane of a patient's tooth. The sides of the tie wings are additional references for alignment with the tooth and are designed for alignment with the long axis of the tooth. The tips of the tie wings are rounded and substantially semicircular. The bracket assembly is made by a machining process. A metal strip is provided and a longitudinal slot corresponding to the archwire slot is machined into the strip. Cuts transverse to the slot are machined to define tie wings having angular corners. The angular tie wing tips are rounded using a die assembly to form a metal strip having a number of tie wings with rounded tips. One tie wing or a pair of adjacent tie wings are sheared from the metal strip and attached to a base pad to form an orthodontic bracket assembly.

17 Claims, 2 Drawing Sheets

U.S. Patent  Apr. 11, 1989  4,819,316 the invention relates to a process for making an orthodontic bracket assembly. In particular, the invention relates to a method for making such an assembly having rounded tie wing tips by a machining process and an orthodontic bracket assembly made from such a process.

METHOD OF MAKING A PRE-ADJUSTED ORTHODONTIC BRACKET ASSEMBLY

FIELD OF THE INVENTION

This invention relates to a process for making an orthodontic bracket assembly. In particular, the invention relates to a method for making such an assembly having rounded tie wing tips by a machining process and an orthodontic bracket assembly made from such a process.

BACKGROUND OF THE INVENTION

A number of orthodontic assemblies for correcting the alignment of teeth for aesthetic or functional deficiencies are known. Generally, such assemblies are attached to individual teeth and provide a bracket for an archwire. One type of bracket assembly is attached to teeth by a band which circles the tooth and has the bracket on the outside of the tooth. A second, more recent, type of assembly has a bonding pad which is attached to a tooth by an adhesive. Typically, this type of assembly has a base for attachment to a bonding pad on the tooth. Attached to the base are two tie wings having a generally T-shaped cross section which are attached to the base at the bottom of the "T". The tie wings are typically attached to the base in a parallel orientation and have cross-wise slots for placement of an archwire.

In use, a number of such brackets are attached to individual teeth. An archwire is fitted into the cross-wide slots and fixed in position using the wire ends. The archwire provides a desired directional force which is transmitted through the brackets to the teeth for re-aligning the teeth.

Previously, such brackets were generally rectangular in shape and the cross-wise slot was disposed at right angles to the sides of the tie wings. With such brackets, however, the archwire had to be bent in between the brackets to obtain the desired tooth realigning pressure. This method of use presented problems when replacing the archwire because reproduction of the bending in the archwire was difficult and caused difficulties with obtaining a continuous uniform force on teeth.

This difficulty was addressed by Andrews in U.S. Pat. No. 3,477,128. Andrews discloses that the cross-wise slots in orthodontic brackets could be cut at non-right angles with respect to the sides of the bracket assembly. In this manner, an unbent or "passive" archwire can be used to impart the necessary realigning force to teeth.

This type of apparatus, however, presented two problems: (1) inaccurate alignment of the bracket on the tooth and (2) weakened tie wings. Each tooth has a preferred angle between the long axis of the tooth and the occlusal plane of the mouth. In the general method of realigning teeth using orthodontic brackets, the cross-wise slot is aligned parallel to the occlusal surface of a patient's tooth. As a realigning pressure is applied to the tooth, the occlusal surface of the tooth is moved into alignment with the occlusal plane of the mouth. If an angled cross-wise slot is provided in a bracket having an otherwise rectangular outline, the only reference line for positioning the cross-wise slot parallel to the occlusal plane of the tooth is the slot itself. Such brackets are difficult to position easily and quickly on a patient's tooth.

The other problem presented by the use of angled cross-wise slots is weakening of portions of the tie wings. If two aligned angled cross-wise slots are provided through a pair of the wings on a bracket assembly having a rectangular outline, the cross slot in each tie wing will be located off center on the tie wing. Such tie wings have portions of the tie wing above and below the cross-wise slot having different thicknesses or amounts of tie wing material, and therefore, are of different strengths. As a force is produced by the archwire and transmitted through the bracket to the tooth, the weaker end of each tie wing is more likely to become damaged by the archwire force.

In U.S. Pat. No. 4,415,330, to Daisley, these problems were addressed by an orthodontic bracket design. The orthodontic bracket assembly in Daisley has a pair of tie wings which form a rhomboidal configuration having archwire slots which bisect the tie wings so that the tie wing tips on either side of the slot are of equal size. In this manner, planes formed by the tops and bottoms of the tie wings are parallel with the archwire slot and can be used for alignment with the occlusal surface of a patient's tooth. Also, because the tie wings are bisected by the archwire slots, the portions of the tie wing above and below the slot are of equal size and equal strength. Because the tie wings have a rhomboidal configuration, the tips of the tie wings have angular outside corners and flat top and bottom surfaces.

A line of orthodontic bracket assemblies, which is currently commercially available and identified by the trademark "The Master Series", is based on U.S. Pat. No. 4,415,330. The brackets of these assemblies have a rhomboidal configuration and are manufactured using a machining process rather than a molding or casting process.

FIGS. 6 and 7 in U.S. Pat. No. 4,415,330, which are designated as "prior art", illustrate two types of orthodontic brackets for use with a passive archwire. These brackets do not satisfactorily address or solve problems relating to alignment with the occlusal plane and weakened tie wing tips due to angled cross-wise slots. The tie wings of these bracket assemblies have angular corners on the tips. These two types of brackets are also known to be made by a machining process, rather than by a molding or casting process.

Another orthodontic bracket assembly currently available is identified by the trademark "SinterLine." Such bracket assemblies have a pair of tie wings having curved outside edges on the tie wings and substantially rounded wing tips. These brackets are designed for improved aesthetic appearance as well as increased patient comfort due to a smoother rounded apparatus. The SinterLine orthodontic brackets are manufactured by a method of casting or molding. The assemblies manufactured by such processes are generally relatively more expensive than those produced by machining techniques, particularly in the case in which a workable machining capability is already available.

Although many differently configured orthodontic brackets have been utilized, it would still be advantageous to provide a relatively inexpensive bracket that is acceptable to the orthodontic practitioner and is also comfortable for the wearer. Accordingly, it is an object of the present invention to provide an orthodontic bracket assembly having a smooth rounded configuration for increased patient comfort which is manufactured by a machining process, rather than a casting or molding process. It is a further objective of the invention to provide an orthodontic bracket assembly which has multiple references for alignment and which has archwire slots bisecting the tie wings.

SUMMARY OF THE INVENTION

The present invention is directed toward improved orthodontic bracket assemblies having rounded tie wing tips and a method for making the assemblies. The bracket assemblies of the present invention include a base pad and one or two tie wings. The base pad is substantially planar and has a relatively smooth side and a textured side. The assembly is attached to the labial side of a patient's tooth by an adhesive placed on the textured side of the base pad. The tie wings are attached to the smooth side of the base pad.

Each tie wing has a substantially T-shaped cross-section, and is attached to the base pad at the bottom of the T-shaped configuration. Each tie wing inludes a body portion and rounded gingival and occlusal tips. The rounded tips are essentially semi-circular in shape and extend outwardly from the body portion. The rounded tips are defined by a diameter substantially equal to the width or lateral extent of the body portion. The extent of each rounded tip in a longitudinal direction is less than the length of the body portion with which it is an integral part of. An archwire slot is formed in the top surface of the body portion of each tie wing for receiving an archwire to impart pressure to a tooth. The assembly is positioned on a patient's tooth by aligning the archwire slot with the occlusal surface of the tooth. As an additional reference for this alignment, a groove is formed in the top surface of the body portion of each tie wing. The groove is substantially parallel to the archwire slot.

The body portion of each tie wing has mesial and distal sides which are substantially transverse to the archwire slot. The mesial and distal sides of each body portion are straight and substantially parallel. The sides are displaced from a line perpendicular to the archwire slot by a predetermined angle. This angle is equal to the ideal angle between the long axis of a patient's tooth and a line perpendicular to the occlusal plane of a patient's mouth. Such a relationship between the side of the tie wing body portion and the archwire slot facilitates alignment of the assembly on a tooth because when the archwire slot is aligned with the occlusal surface of the tooth, the sides of the tie wing body portion will be aligned with the long axis of the tooth. As a result, each side can serve as an additional reference for alignment of the bracket on the tooth.

In the case of a pair of tie wings, the bracket assembly can further include a ridge positioned between two tie wings which is substantially parallel to the tie wing sides. The ridge serves as an additional reference for alignment of the assembly with the long axis of the tooth.

In making the orthodontic bracket assembly using a machining process, an elongated metal strip is provided. A longitudinal slot corresponding to the archwire slot and a longitudinal groove corresponding to the aligning groove are machined into the strip. Transverse crosswise cuts are machined in the strip to define the tie wings. The cross-wise cuts produce tie wings having tips with sharp angular corners. The present invention further includes a method for rounding the tie wing tips using a die assembly having top and bottom die pieces. The bottom die piece has a platform for supporting the metal strip having angular tie wings. The platform includes a groove for receiving the bottom portion of the metal strip and rounded supports for supporting the tie wing tips. When the metal strip is in position on the bottom die, the tie wing tips are partially supported by the rounded supports with the angular portions extending over the supports. The tie wing tips are rounded by closing the top die piece over the bottom die piece to shear off the angulr portions of the tie wings to produce a metal strip having tie wings with rounded tips. Single tie wings or pairs of the tie wings are cut from this strip and attached to base pads to form finished orthodontic bracket assemblies.

DETAILED DESCRIPTION

The present invention relates to an orthodontic bracket assembly and a process for making the assembly. The bracket assembly is used for applying directional forces to a patient's tooth with an archwire for realigning teeth. The bracket assembly is attached to a patient's tooth with a base pad on the labial side of the tooth. The bracket assembly further includes one or two tie wings connected to the base pad. An archwire slot is formed cross-wise through each of the tie wings. A series of such bracket assemblies are attached to a patient's teeth. An archwire is placed in the archwire slot of each assembly and it is anchored at the ends of the archwire. In this manner, directional forces are produced on individual teeth.

Figure 5:
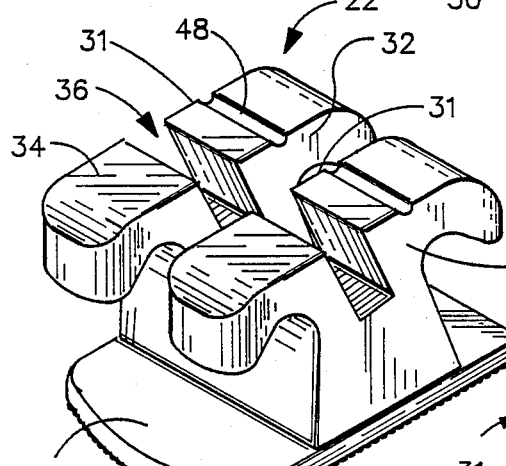
FIG. 5 is a perspective view of a bracket body containing a pair of wing tips affixed to the smooth side of a base.
Figure 6:
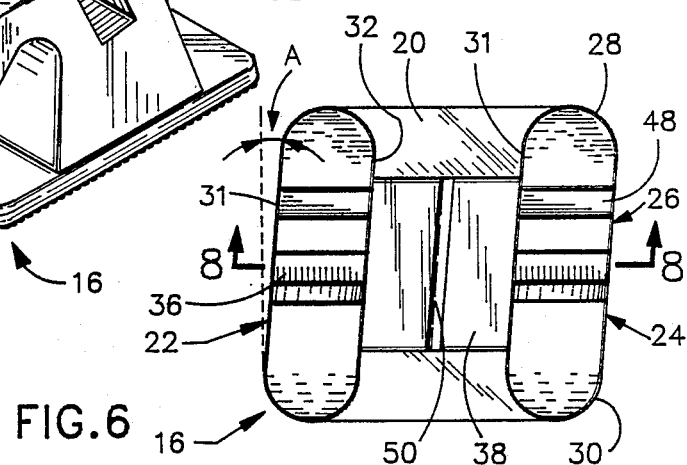
FIG. 6 is a top view of the bracket of FIG. 5.

With reference to FIGS. 5 and 6, an embodiment of the bracket assembly 16 is illustrated. The assembly 16 includes a generally flat base pad 20 and a pair of tie wings 22, 24 attached to one face of the base pad 20. The tie wing 22 is a mesial tie wing and the tie wing 24 is a distal tie wing. An orthodontic bracket assembly 16 in accordance with the present invention can include one or two tie wings, and if two tie wings are provided, they are positioned in a side-by-side fashion as shown in FIG. 5.

Figure 7:
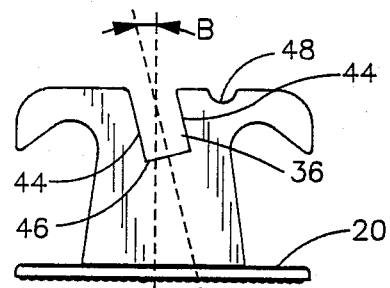
FIG. 7 is a cross-sectional view through the wing tips of the bracket of FIG. 5.

Each tie wing has a generally T-shaped cross section as shown in FIG. 7. With reference to FIGS. 5 and 6, each tie wing 22, 24 includes a body portion 26 and a pair of rounded tips 28, 30. The rounded tip 28 is a gingival tip and the rounded tip 30 is an occlusal tip. Each body portion 26 has a mesial side 31 and a distal side 32. The mesial and distal sides 31, 32, respectively, are substantially straight and parallel to each other. Each of the two rounded tips 28, 30 is integral with its respective tie wing body portion 26. Each tie wing 22, 24 has a top surface 34 which slopes toward the base pad 20 at either end. With further reference to FIG. 7, the portion of each tie wing 22, 24 attached to the base pad 20 is somewhat enlarged in cross section and becomes more narrow in the direction away from the base pad 20. The rounded tie wing tips 28, 30 extend out beyond the portion of the tie wing attached to the base pad 20. On bracket assemblies having two tie wings, all four tie wing sides are substantially parallel.

Each rounded tie wing tip 28, 30 is substantially semicircular in shape. The diameter of the semicircular portion is at least equal to the width of the body portion 26 of the tie wing. If the diameter of the semi-circle is exactly equal to the width of the body portion 26, the mesial 31 and distal 32 sides of the body portion 26 connect tangentially to their respective rounded tips 28, 30. If the diameter of each of the semi-circular tips 28, 30 is greater than the width of the body portion 26, the tip is less than a complete semi-circle. As the diameter of each of the rounded tips 28, 30 increases, the tips flatten out, and eventually have a generally rectangular shape. It is an object of the present invention to provide substantially rounded tie wing tips 28, 30 for increased patient comfort. Accordingly, while the diameter of each of the rounded tips 28, 30 may be greater than the width of the body portion 26, the diameters are sufficiently close to the width of the body portion 26 to provide a generaly semi-circular shape. The diameter of each of the rounded tips 28, 30 cannot be less than the width of the body portion 26. Otherwise, sharp corners are created at the portions of the tie wing connecting the mesial 31 and distal 32 sides of the tie wings to the semi-circular rounded tips 28, 30. The rounded shape on the tips 28, 30 of the tie wings 22, 24 provide improved patient comfort and a more aesthetically pleasing appearance.

Each tie wing 22, 24 has a longitudinal axis. The rounded tips 28, 30 extend along a portion of the length of this axis while the body portion 26 extends along the remainder of this axis. The portion of the length of tie wings 22, 24 which consists of the rounded tips 28, 30 is equal to two times the radius of one of the rounded tips 28, 30 and as discussed above, the diameter of each of the rounded tips 28, 30 is equal to the width of the body portion 26. In a preferred embodiment of the present invention, the ratio of length of body portion 26 to combined rounded tie wing tip length is about 2.33.

The length of the tie wings 22, 24 is primarily a function of providing sufficient structure for ligating an archwire to the bracket assembly. In use, a number of bracket assemblies are attached to a patient's teeth and an archwire is positioned in the archwire slot 36 of each assembly. The archwire slot 36 is positioned generally transverse to the mesial 31 and distal 32 sides of the tie wings. As illustrated in FIG. 6, for a bracket assembly having two tie wings, the archwire slots 36 in the two tie wings are aligned. The archwire slot 36 is cut into the top 34 of the tie wings to a depth and width sufficient to retain an archwire placed in the slot 36. More particularly, the slot 36 generally extends into the tie wing to a depth approximately below the tie wing tips. To secure the archwire in the slot 36, some form of ligature is provided. For example, a common type is a small elastic band which is substantially donut shaped. After an archwire is placed in the archwire slot 36, the band is placed over a first tie wing tip and stretched over the labial surface of the archwire. The band is then placed over the second tie wing tip to secure the archwire in place. An alternative ligature is a wire positioned on the tie wing in the same manner as the elastic band.

For the tie wing to provide an effective structure for ligation of the archwire, the tie wing tips 28, 30 must extend longitudinally beyond the portion of the tie wing 22, 24 attached to the base pad 20. Additionally, the tie wing tips 28, 30 are provided, as seen in FIG. 7, to extend toward the base pad 20. In this manner, as ligature is placed on the underside of the tie wing, the ligature is less likely to accidentally become undone.

As depicted in the drawings, the mesial 31 and distal 32 sides of the tie wings are substantially perpendicular to the plane of the base pad 20. The mesial 31 and distal 32 sides connect and are integral with the round surfaces of the rounded tie wing tips 28, 30. The mesial side 31 of the mesial tie wing 22 extends from the connection of the base pad 20 with the tie wing 24 to the top surface 34 of the tie wing 22. The distal side 32 of the mesial tie wing 22, however, extends from the top surface 34 of the tie wing 22 to a connecting portion 38 of the bracket assembly connecting the mesial 22 and distal 24 tie wings. Likewise, the mesial side 31 of the distal tie wing 24 extends only from the top surface 34 of the tie wing 24 to the connecting portion 38. The distal side 32 of the distal tie wing 24 extends from the top surface 34 of the tie wing 24 to the connection of the tie wing with the base pad 20.

In attachment of a bracket assembly to a patient's tooth, the parallel mesial sides 31 and distal sides 32 are particularly useful as a reference for aligning the bracket assembly on the tooth. The bracket assembly, as discussed in more detail below, is manufactured so that when the mesial 31 and distal 32 sides of the tie wings are aligned parallel with the long axis of the tooth, the archwire slot 36 is in proper alignment for the archwire to create a particular desired directional force on the tooth.

As discussed above, each tooth has an ideal position in a patient's mouth which is defined by a given angle between the long axis of a tooth and a line perpendicular to the occlusal plane of the mouth. This angle varies for different teeth. The bracket assemblies 16 are provided so that a line perpendicular to the longitudinal axis of the archwire slot is offset from the sides of the tie wings 22, 24 by an angle A, shown in FIG. 6. The present bracket assembly is designed such that the angle A is equal to the given angle for the tooth for which the bracket assembly is designed. In this manner, as the mesial side 31 and the distal side 32 of the tie wings 22, 24 are aligned with the long axis of a patient's tooth, the archwire slot 36 is aligned parallel with the occlusal surface of the patient's tooth. When a bracket assembly 16 is placed on a misaligned tooth, the archwire slot 36, being aligned with a occlusal surface of the tooth, is not aligned with the occlusal plane of the mouth. An archwire is placed in the slot of the bracket assembly 16 and tension in the archwire is created by attaching the ends of the wire to molars. The tension in the wire tends to force the archwire slot, and concomitantly, the occlusal surface of the tooth, into alignment with the occlusal plane of the mouth. When this position is achieved the tension from the archwire on the bracket is relieved.

As illustrated in Figure slot 36, are of relatively equal thickness and strength. In this manner, as the pressure created by the archwire is transmitted through the bracket assembly to the tooth for realignment of the tooth, the gingival and occlusal portions of the tie wing are equally likely to resist damage from the pressure.

The tie wings 22, 24 of the bracket assembly 16 further define a groove 48 on the top surface 34 of the tie wing. The groove 48 is illustrated in FIGS. 5 and 7. The groove 48 provides a referre slot 36, are of relatively equal thickness and strength. In theis manner, as the pressure created by the archwire is transmitted through the bracket assembly to the tooth for realignment of the tooth, the gingival and occlusal portions of the tie wing are equally likely to resist damage from the pressure.

The tie wings 22, 24 of the bracket assembly 16 further define a groove 48 on the top surface 34 of the tie wing. The groove 48 is illustrated in FIGS. 5 and 7. The groove 48 provides a reference for alignment with the occlusal surface of the tooth in addition to the archwire slot 36. Accordingly, the groove 48 is substantially parallel to the archwire slot 36.

As seen in FIGS. 5 and 7, the groove 48 is generally curved and runs transverse to the mesial 31 and distal 32 sides of the tie wings 22, 24. The groove 48 has an inside edge on the top surface 34 of the tie wing and an outside edge on the top surface 34 of the tie wing. The inside edge is that edge nearest to the archwire slot and the outside edge is that edge nearest to the tie wing tip. The depth of the groove 48 is not critical to the functioning of the bracket assembly. The groove 48 is used as a visual reference, and therefore, is deep enough to be visible when positioning brackets on a patient's tooth. The groove 48 is positioned on the top surface 34 of the tie wing and extends from the mesial side 31 to the distal side 32 of the tie wing. The groove 48 is sufficiently close to the center portion of the tie wing and the archwire slot 36 so that the outside edge of the groove 48 is not shortened by rounding of the tie wing tips.

Figure 8:
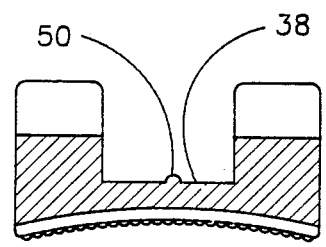
FIG. 8 is a cross-sectional view of the bracket taken along lines 8—8 of FIG. 6.

With reference to FIGS. 6 and 8, a ridge 50 is provided on bracket assemblies having two tie wings. The ridge 50 is positioned on the connecting portion 38 of the bracket assembly between the tie wings. The ridge 50 is raised and has a generally semi-circular cross section, as seen best in FIG. 8.

The ridge 50 is useful as an additional reference for aligning the bracket assembly on a patient's tooth with respect to the long axis of the tooth. The ridge 50 should be sufficiently large to be visible to an orthodontist applying the bracket assemblies. The ridge 50 is aligned on the connecting portion 38 of the bracket assembly in an orientation substantially parallel to the mesial sides 31 and distal sides 32 of the tie wings.

With reference to FIG. 5, the base pad 20 of the bracket assembly 16 is a thin substantially planar element having top and bottom surfaces. The tie wing or pair of tie wings are attached to the top surface of the base pad 20 which is relatively smooth. On the bottom portion of the base pad 20, the surface is textured, as seen in FIGS. 5, 7 and 8. The textured surface facilitates adhesion between the bracket assembly and a patient's tooth as the assembly is attached with an adhesive. The bottom surface of the base pad 20 can have various textures, including but not limited to, a ridged or corrugated surface. As seen in FIG. 6, the base pad 20 does not extend beyond the outside portions of the tie wings. A smaller base pad 20 aids in patient comfort by not interfering with the patient's gingiva or mastication.

Figure 1:
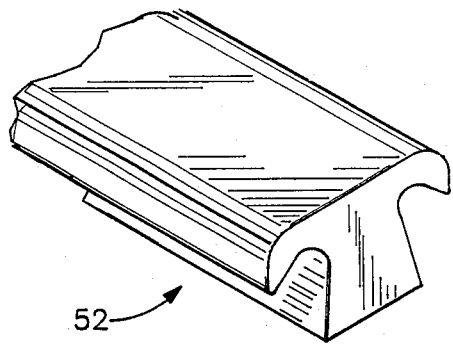
FIG. 1 is a perspective view of an elongated metal strip from which tie wings are machined.

To manufacture the above-described orthodontic bracket assembly, an elongated strip of metal 52, as depicted in FIG. 1, is provided. The strip 52 is machined to define the tie wings, the cross slots, the groove, and the ridge of the bracket assemblies. Pairs of tie wings are sheared from the strip 52 and attached to base pads to form finished bracket assemblies. The metal strip 52 can be made of metals commonly used in orthodontics.

In cross section, the metal strip 52 has a generally T-shaped configuration consisting of a top portion, corresponding to the cross bar of the T and a bottom portion corresponding to the base of the T. The top surface of the cross section is generally flat in the central portion of the top section and gradually slopes downward at either end. The ends of the top portion are enlarged and extend downward. The bottom portion of the T-shaped cross section is broader at the base of the bottom portion than at the connection with the top portion.

Figure 2:
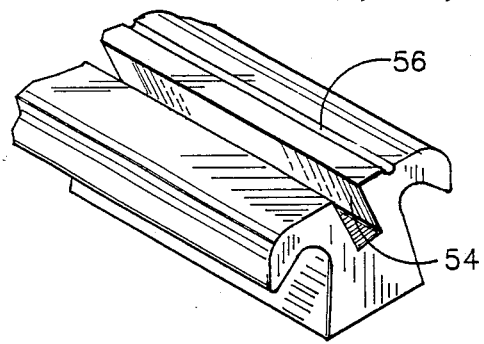
FIG. 2 is a perspective view of a metal strip in which two longitudinal strips have been machined, one of which is to serve as the archwire slot, and the other as an indicator groove in the finished bracket.

With reference to FIG. 2, a longitudinal slot 54 is machined into the metal strip 52. The archwire slot 36 in the finished bracket assembly 16 corresponds to a portion of this longitudinal slot 54. The longitudinal slot 54 is cut into the top surface of the metal strip 52 in an orientation generally parallel to the longitudinal axis of the metal strip 52.

As seen in FIG. 2, the longitudinal slot 54 is cut into the top surface of the metal strip 52 substantially in the center of the top surface. In this manner, the top portions of the metal strip on either side of the longitudinal slot 54 are of relatively equal thickness.

As depicted in FIG. 2, the longitudinal slot 54 is cut into the metal strip 52 through the top portion of the strip 52 and into the bottom portion. The longitudinal slot 54 is cut to a depth sufficient so that, as an archwire is fitted into the archwire slot 36 of a finished bracket assembly, the archwire is securely held in place.

As discussed above, the sides of the archwire slot 44 are positioned at an angle B with respect to a line perpendicular to the base pad 20. Accordingly, the sides of the longitudinal slot 54 are angled so that as the tie wings 22, 24 are formed from the metal strip 52, the sides of the archwire slot 44 are correctly angled.

With further reference to FIG. 2, a longitudinal groove 56 is provided on the top surface of the metal strip 52. The groove 48 in the finished bracket assembly 16 corresponds to a portion of the groove 56. Accordingly, the longitudinal groove 56 is a shallow rounded groove cut into the top surface of the metal strip 52. The longitudinal groove 56 is positioned parallel to the longitudinal axis of the metal strip 52 and is also parallel to the longitudinal slot 54. The longitudinal groove 56 is positioned close enough to the longitudinal slot 54 so that in subsequent steps during which tips of the tie wings are rounded, the grooves 48 in the tie wings 22, 24 are not impaired or cut.

Figure 3:
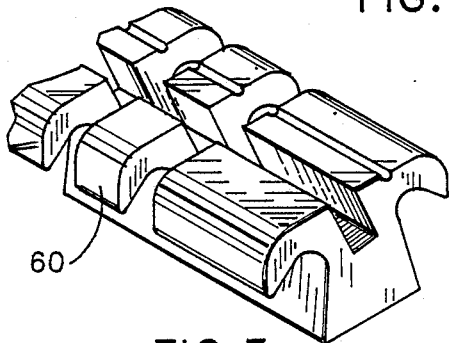
FIG. 3 is a perspective view of the metal strip of FIG. 2 after machining to define tie wings with angular tips.

The metal strip 52 having a longitudinal slot 54 and a longitudinal groove 56 is machined by cross-wise cuts to define a number of unfinished tie wings 22, 24. With reference to FIG. 3, cuts transverse to the longitudinal axis of the metal strip produce a series of attached unfinished tie wings 22, 24. The sides of these tie wings 22, 24 correspond to the mesial side 31 and the distal side 32 of finished tie wings 22, 24. The unfinished tie wings have generally angular, or non-rounded, tie wing tips 60.

The metal strip 52 is machined transversely at distances along the metal strips 52 such that the resulting unfinished tie wings 22, 24 are of a width equal to the desired width of a finished tie wing. The transverse machining of the metal strip is also conducted in such a manner to produce pairs of unfinished tie wings 22, 24 spaced a distance apart equal to the desired spacing between two tie wings 22, 24 in a finished tie wing pair.

The cross-wise cuts machined into the metal strip 52 extend through the top portion of the metal strip 52 approximately midway into the bottom portion of the metal strip 52 to form connecting portions 38 between tie wings 22, 24. For two adjoining unfinished tie wings 22, 24 which correspond to a pair of finished tie wings 22, 24 for one bracket assembly 16, this connecting portion corresponds to the connecting portion 38, as shown in FIG. 6.

The step of machining transverse cuts into the metal strip 52 determines the angle of the tie wing sides 31, 32 in the finished bracket assembly with respect to the archwire slot 36. For orthodontic bracket assemblies of the type in the present invention, the archwire slot 36 is aligned with the occlusal surface of the tooth as the assembly is attached to the tooth. Given this condition, sides of the tie wings 31, 32 can be provided at various angles without affecting the functional effectiveness of the bracket. However, it is desirable to provide tie wings having sides 31, 32 disposed at an angle relative to the archwire slot 36 such that the sides 31, 32 are useful for aligning the bracket on a patient's tooth. Accordingly, the transverse cuts into the metal strip 52 forming the tie wing sides are made so that, when the archwire slot 36 is aligned with the occlusal surface of the tooth, the tie wing sides 31, 32 are aligned with the long axis of the tooth. The tie wings sides 31, 32 thereby function as an additional reference for aligning each of the tie wings 22, 24.

It is contemplated that during the transverse machining step, the ridge 50 between a pair of tie wings 22, 24 on a bracket assembly 16 having two tie wings can be machined by using a different cutting piece. To form a transverse cut without a ridge, a cutting piece having a substantially rectangular cross section is used. To form a transverse cut with a ridge, a cutting piece having a substantially rectangular cross section with a rounded concave portion centrally positioned along the bottom side of the cross section is used. As discussed above, the ridge 50 has a generally semi-circular cross section and is positioned parallel to the sides 31, 32 of each of the tie wings 22, 24.

Figure 4:
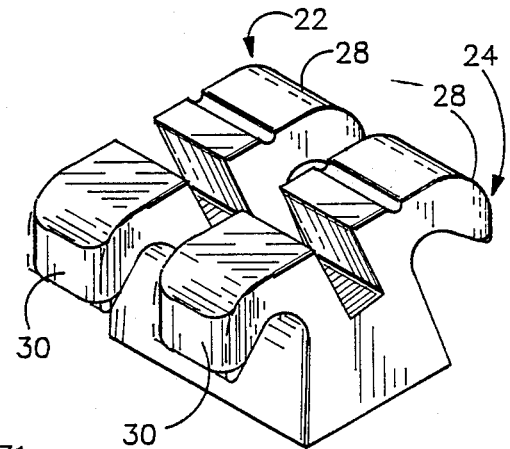
FIG. 4 is a perspective view of a pair of wing tips severed from the metal strip, illustrating the rounding of angular tips of tie wings.

As illustrated in FIG. 3, the tie wings 22, 24 formed by these machining steps, have generally angular tips 60. In accordance with the present invention, the angular tips 60 of the tie wings on the metal strip are rounded by a machining process. With reference to FIG. 4, a pair of tie wings 22, 24 having rounded tie wing tips 28, 30 are illustrated. The shape of the angular wing tips prior to the rounding step are shown in outline.

Figure 9:
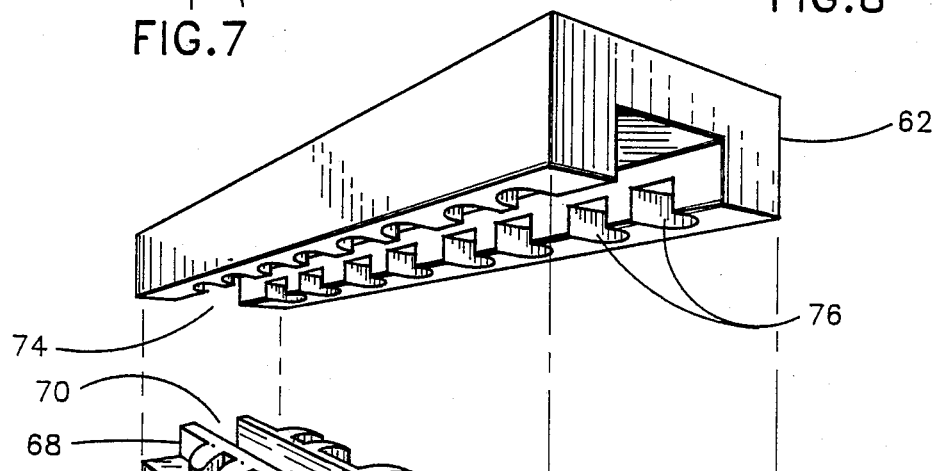
FIG. 9 is a perspective view of the top and bottom members of the die apparatus.

With reference to FIG. 9, the die apparatus for rounding angular wing tips is illustrated. The apparatus includes a top die 62 and a bottom die 64. With reference to FIG. 9, the bottom die 64 has a base portion 66 and a platform portion 68. The base portion 66 is generally rectangular in shape and supports the platform portion 68. The platform portion 68 is raised above the base portion 66 and is generally elongated in shape. The platform portion 68 includes a work piece channel 70 extending the length of the platform 68. The channel 70 is sufficiently wide so that the bottom portion of the metal strip 52 fits into the channel 70. The depth of the channel 70 is great enough so that as the metal strip 52 is placed in the channel 70, the bottom portion of the metal strip 52 extends into the channel 70 and the top portion of the metal strip 52 rests on the platform portion 68.

As further depicted in FIG. 9, the platform portion 68 of the bottom die 64 further includes rounded supports 72. The rounded supports 72 extend away from the work piece channel 70 on either side of the platform portion 68. The rounded supports 72 are provided so that as a work piece is placed into the work piece channel 70, each of the unfinished tie wings 22, 24 of the work piece having tie wing tips 60 with angular corners aligns with and is supported by a rounded support 72. Accordingly, the rounded supports 72 are generally provided in pairs along either side of the platform portion 68 to correspond with pairs of tie wings on the metal strip 52 to be formed into bracket assemblies. As illustrated in FIG. 9, each pair of rounded supports 72 on one side of the work piece channel 70 corresponds with a pair of rounded supports 72 on the opposite side of the work piece channel 70. These pairs of rounded supports 72 are offset from the corresponding pair of rounded supports 72 on the opposite side of the work piece channel 70. This alignment of rounded supports 72 is necessary to provide support for a work piece having pairs of tie wings disposed at angles with respect to the longitudinal axis of the work piece.

With further reference to FIG. 9, the top die 62 is illustrated. The top die 62 is a generally concave piece which fits over the platform portion 68 of the bottom die 64. Accordingly, the top die 62 defines a generally elongated groove 74. Spaced along the sides of this elongated groove 74 are generally rounded pairs of concave depressions 76 corresponding in a mating fashion to the rounded supports 72 of the bottom die 64.

The rounded concave depressions 76 are cutting surfaces which round the tie wing tips 28, 30 as the top die 62 is pressed over the bottom die 64. As discussed above, the diameter of each of the rounded tie wing tips 28, 30 is equal to at least the width of the body portion 26 of each of the tie wings 22, 24. To form a rounded tip having a diameter with this limitation, the concave depressions 76 which form the rounded tips 28, 30 must have a diameter at least equal to the width of the body portion 26 of the tie wing. This diameter is determined by adding to the specification width of the tie wings the margin of error in the machining process to form the tie wings. This width is equal to the maximum possible width of a tie wing. By providing a top die 62 with rounded depressions 76 having a diameter equal to the maximum possible width of the tie wing, the diameter of the rounded tips 28, 30 of a tie wing will be at least equal to the width of the body portion 26 of the tie wing.

The length of a tie wing prior to rounding is equal to the width of the top portion of the metal strip 52. At most, the length of the rounded tie wing can be equal to the length of the unrounded tie wing by rounding only the angular corners without removing material from the apex of the semi-circle. As discussed above, the primary function of the portions of the tie wing extending over the base pad 20 is to provide a structure for ligature. Accordingly, during the rounding process it is possible to shorten the tie wing if sufficient structure remains after shortening for ligature. However, initially providing a metal strip 52 having a top width equal to the desired tie wing length is simpler and more economical than shortening the tie wing during the rounding process. Accordingly, each pair of concave depressions 76 of the top die 62, which form the cutting surfaces for rounding the tie wing tips, are spaced apart from each other a distance such that the distance between the deepest point in each concave groove 76 is approximately equal to the length of the unrounded tie wing. In this manner, as tie wing tips are rounded, the tie wings are not shortened.

In operation, a work piece having pairs of tie wings with generally angular tie wing tips 60 is positioned in the workpiece channel 70 of the bottom die 64. The angular tie wing tips 60 are aligned over the rounded supports 72 of the bottom die 64. In this position, portions of the tie wing tips 60 are supported by the rounded supports 72. The angular portions of the tie wing tips 60, however, extend over the rounded supports 72.

The top die 62 and the bottom die 64 are pressed together with the rounded depressions 76 and the rounded supports 72 in alignment. As the top die 62 closes over the platform portion 68 of the bottom die 64, the portions of the elongated groove 74 which define the rounded depressions 76 contact the angular portions of the tie wing tips 60 extending over the rounded supports 72. As the top die 62 and the bottom die 64 close further, the portions of the elongated groove 74 in contact with the angular corners of the tie wings shear the angular corners from the remainder of the tie wings which are supported by the rounded supports 72. After the angular corners 60 of the tie wings 22, 24 have been sheared to form tie wings having rounded tips 28, 30, the top die 62 and the bottom die 64 are moved apart and the work piece is removed from the work piece channel 70.

The resulting product is a strip of tie wing pairs 22, 24 with each having rounded tie wing tips 28, 30. The underneath sides of the rounded portions of the tie wing tips generally have burrs or rough edges created by the shearing action of the concave depressions 76. These burrs are smoothed or polished in any conventional manner known to the art.

Pairs of tie wings or single tie wings for orthodontic bracket assemblies having two or one tie wings, respectively, are prepared from the work piece by shearing pairs of or single tie wings from the strip. Each pair of tie wigs or single tie wing is attached to a base pad 20 to form an orthodontic bracket assembly. Such attachment can be done by brazing the two pieces of metal together.

It is apparent from the above discussion that bracket assemblies adapted for use with particular teeth have tie wings positioned with respect to the archwire slot 36 at different angles. Such bracket assemblies necessitate the use of different die pieces. The angles at which pairs of rounded supports 72 are offset depend upon the angle at which the tie wing to be rounded by the die apparatus is positioned with respect to the archwire slot 36. Accordingly, it is an aspect of the present invention to provide die assemblies adapted for rounding angular wing tips 60 of tie wings for bracket assemblies suitable for every tooth in a patient's mouth. Such die assemblies have pairs of rounded supports 72 on either side of the work piece channel 70 offset at different angles. Correspondingly, each such die apparatus has a top die 62 with an elongated groove 74 defining pairs of rounded depressions 76 on either side of the groove 74 offset at angles corresponding to those of the rounded supports 72 on the bottom die 64.

Figure 10:
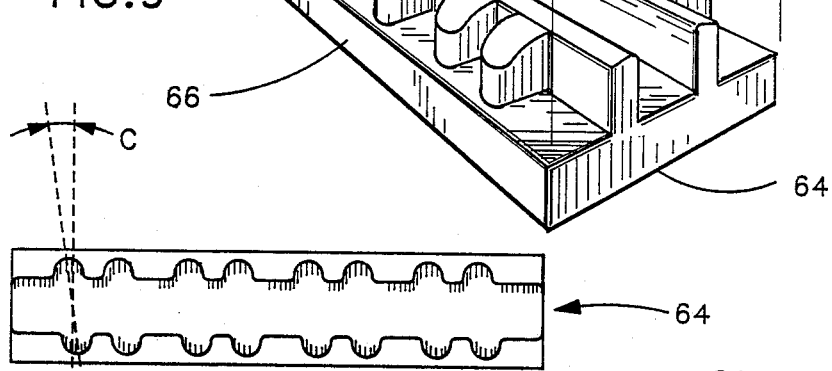
FIG. 10 is a bottom view of the top die member, with opposing cutting means offset from one another by angle C.
Figure 11:
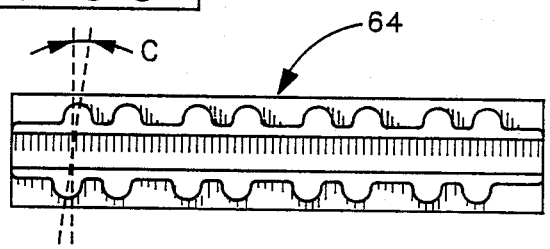
FIG. 11 is a top view of a bottom die member, with the opposing rounded supports offset from one another by angle C.

With reference to FIG. 10, a bottom view of a top member is illustrated. The opposing rounded cutting means 76 are offset from one another at a given angle C. FIG. 11 illustrates the top view of the bottom die member corresponding to the top member of FIG. 10. The opposing rounded supports 72 of FIG. 11 are offset from one another at the same angle C. The cutting means 76 of FIG. 10 correspond in mating fashion to the support means 72 of FIG. 11.

Each tooth on the right side of a patient's mouth has a corresponding tooth on the left side. The long axis of each tooth in such pairs of corresponding teeth are ideally displaced from a line perpendicular to the occlusal plane of the mouth at an angle of equal magnitude but in a different direction. Accordingly, orthodontic bracket assemblies of the kind in the present invention for such pairs of teeth have tie wings which are disposed relative to the archwire slot 36 of the tie wings at angles of equal magnitude, however, the angles of the tie wings are in different directions. Accordingly, to form such corresponding bracket assemblies, die apparatuses accounting for such differences in configuration are necessary.

In view of the foregoing, numerous advantages over the known references are apparent. An orthodontic bracket assembly is provided having multiple references for alignment of the assembly on a patient's tooth. The sides of the tie wings and a raised ridge situated between the tie wings and parallel to the sides of the tie wings are used for alignment of the bracket assembly with the long axis of the patient's tooth. The archwire slot and a groove disposed on the top surface of the tie wing and substantially parallel to the archwire slot are used for alignment of the bracket assembly on the patient's tooth with respect to the occlusal surface of the tooth. The bracket assembly also provides increased comfort to the patient by providing tie wings having rounded tips for reduced irritation to the inside of a patient's mouth. The above described orthodontic bracket assembly is produced by a machining process which is relatively inexpensive. A number of dies are provided for rounding of tie wing tips of bracket assemblies having tie wings disposed at varying angles with respect to the archwire slot.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A method of making an orthodontic bracket assembly, comprising:
   providing a strip of metal;
   providing a die means, said die means including first and second rounded cutting means, wherein each said first cutting means is positioned offset from each said second cutting means at a first angle;
   machining said metal strip to define a slot along the longitudinal extent of said metal strip;

machining said metal strip to define a number of tie wings, each of said tie wings having a pair of tips with substantially angular corners;

rounding said substantially angular corners by machining at least some of said tips using said die means; and severing at least one of said tie wings from said metal strip.

2. A method, as claimed in claim 1, further including:
forming a raised indicating marker on said bracket, said marker being substantially parallel to the longitudinal axis of said tie wings.

3. A method, as claimed in claim 1, wherein:
said rounding step includes forming rounded tips from the tips of at least one of said tie wings, said rounded tips having a substantially semi-circular shape.

4. A method, as claimed in claim 3, further including:
forming an indicator groove in a portion of at least one of said tie wings separate from said portion of said tie wing having said semi-circular shape.

5. A method, as claimed in claim 1, wherein:
said machining step includes the step of forming said longitudinal slot wherein said slot bisects each of said tie wings.

6. A method as claimed in claim 5, wherein:
said machining step includes the step of providing said tie wings at a predetermined angle with respect to a line perpendicular to said longitudinal slot.

7. A method, as claimed in claim 6, wherein:
said providing step includes the step of forming said predetermined angle wherein said predetermined angle is equal to an ideal angle between a line perpendicular to the occlusal plane of a patient's mouth and the long axis of a predetermined tooth.

8. A method of making an orthodontic bracket assembly, comprising:
providing an elongated strip of metal;
machining said metal strip to define a slot along the longitudinal extent of said metal strip;
machining said metal strip to define a number of tie wings, each of said tie wings positioned substantially transverse to the longitudinal axis of said metal strip at a predetermined angle and each of said tie wings having a pair of tips with substantially angular corners;
rounding said substantially angular corners of at least some tie wings with die means, said die means having pairs of substantially semi-circular cutting pieces;
severing at least one of said tie wings from said metal strip.

9. A method, as claimed in claim 8 wherein:
said metal strip is positioned relative to said die means in a first position and each of said pairs of cutting pieces defines a cutting axis positioned at said predetermined angle relative to said longitudinal axis of said metal strip when said metal strip is in said first position.

10. A method of making an orthodontic bracket assembly, comprising:
providing a strip of metal;
providing die means;
machining said metal strip to define a slot along the longitudinal extent of said metal strip;
machining said metal strip to define a number of tie wings, each of said tie wings having a pair of tips with substantially angular corners;
rounding said substantially angular corners by machining at least some of said tips wherein said step of rounding includes engaging at least portions of said tie wing tips with at least portions of said die means; and pressing together said die means to remove said angular corners from at least some of said tie wing tips; and
severing at least one of said tie wings from said metal strip.

11. A method for making a plurality of orthodontic assemblies, each assembly having at least one tie wing and an archwire slot and in which each tie wing of one assembly forms an angle with its respective archwire slot that is different from the angle defined by the tie wing and its respective archwire slot of another assembly, comprising:
providing a first die means, said first die means including first and second rounded cutting means, wherein each said first cutting means is positioned offset from each said second cutting means at a first angle;
forming a first orthodontic bracket assembly having at least a first tie wing with angular tips, said first tie wing having a transverse archwire slot, wherein said first tie wing is positioned with respect to said slot at said first angle;
contacting said first and second cutting means with said first orthodontic bracket assembly to round said angular tips;
providing a second die means, said second die means including third and fourth rounded cutting means, wherein each said third cutting means is positioned offset from each said fourth cutting means at a second angle;
forming a second orthodontic bracket assembly having at least a first tie wing with angular tips, said first tie wing of said second orthodontic assembly having a transverse archwire slot, wherein said first tie wing is positioned with respect to said slot at said second angle; and
contacting said third and fourth cutting means with said second orthodontic bracket assembly to round said angular tips.

12. A method, as claimed in claim 11, wherein:
said first and second die means each comprises top and bottom die members.

13. A method as claimed in claim 12, wherein:
each of said bottom die members comprises a platform, said platforms having a channel for receiving orthodontic bracket assemblies in a first position, wherein when said bracket assemblies are in said first position, said platforms support at least portions of said bracket assemblies.

14. A method as claimed in claim 13, wherein:
said top die means of said first die means includes said first and second rounded cutting means, and said top die means of said second die means includes said third and fourth rounded cutting means.

15. A method, as claimed in claim 14, wherein:
each of said platforms comprise rounded supports and, when said bracket assemblies are in said first position, said angular tips are supported by said rounded supports with angular portions of said tips overhanging said rounded supports.

16. A method, as claimed in claim 15, comprising:
contacting said overhanging angular portions of said tie wing tips with said first and second cutting means.

17. A method, as claimed in claim 15, comprising:
contacting said overhanging angular portions of said tie wing tips with said third and fourth cutting means.

* * * * *